United States Patent [19]
Fornace, Jr. et al.

[11] Patent Number: 5,616,463
[45] Date of Patent: Apr. 1, 1997

[54] METHODS FOR DETERMINING THE PRESENCE OF FUNCTIONAL P53 IN MAMMALIAN CELLS

[75] Inventors: Albert J. Fornace, Jr., Bethesda; Michael B. Kastan, Owings Mill, both of Md.

[73] Assignees: The United States of America as represented by the Secretary Department of Health and Human Services, Washington, D.C.; Johns Hopkins University, Baltimore, Md.

[21] Appl. No.: 288,872

[22] Filed: Aug. 10, 1994

Related U.S. Application Data

[63] Continuation of Ser. No. 974,960, Nov. 12, 1992, abandoned.

[51] Int. Cl.$^6$ .............................. C12Q 1/68; C07H 21/02
[52] U.S. Cl. ................................................ 435/6; 536/23.5
[58] Field of Search ..................................... 435/6; 935/77, 935/78; 436/501; 536/23.5

[56] References Cited

PUBLICATIONS

M.C. Hollander et al., (Nov. 8, 1993) Analysis of the Mammalian GADD45 Gene and its response to DNA Damage; *Chemical Abstracts*, vol. 119, No. 19, pp. 230–231 and *J. Biol. Chem.* (1993) 268:24385–24393.

M.B. Kastan et al., (Feb. 1, 1993) A Mammalian Cell Cycle Checkpoint Pathway Utilizing p53 and GADD45 is Defective in Ataxia–Telangiectasia; *Chemical Abstracts*, vol. 118, No. 5., p. 308 and *Cell* (1992) 71:587–597.

B.D. Price et al., (Aug. 17, 1992) GADD45 and GADD153 Messenger RNA Levels are Increased During Hypoxia and After Exposure of Cells to Agents Which Elevate the Levels of the Glucose–Regulated Proteins; *Chemical Abstracts*, vol. 117, No. 7, p. 561 and *Cancer Res.* (1992) 52:3814–3817.

M.A. Papathanasiou et al., (Sep. 16, 1991) Induction by Ionizing Radiation of the GADD45 Gene Incultured Human Cells: Lack of Mediation by Protein Kinase C; *Chemical Abstracts*, vol. 115, No. 11, p. 419 and *Mol. Cell. Biol.* (1991) 11:1009–1016.

D. Wolf et al., (Nov. 5, 1984) Reconstitution of p53 Expression in a Nonproducer Ab–MuLV–Transformed Cell Line by Transfection of a Functional P53 Gene; *Chemical Abstracts*, vol. 101, No. 19, p. 153 and *Cell*, (1984) 38:119–126.

Kern, et al., Identification of p53 As A Sequence–Specific DNA–Binding Protein; *Science*, 252: 1708–1711 (1991).

Kern et al., Oncogenic Forms of p53 Inhibit p53–Regulated Gene Expression; *Science*, 256:827–830 (1992).

Funk et al., A Transcriptionally Active DNA–Binding Site For Human p53 Protein Complexes; *Mol. Cell Biol.*, 12:2866–2870 (1992).

El–Deiry et al., Definition Of A Consensus Binding Site For p53; *Nature Genet*, 1:45–49 (1992).

Kastan et al., Participation of p53 Protein In The Cellular Response To DNA Damage; *Cancer Res.*, 51:6304–6311 (1991).

Kuerbitz, et al., Wild–Type p53 Is A Cell Cycle Checkpoint Determinant Following Irradiation; *Proc. Natl. Acad.*, 89: 7491–7495 (1992).

Fornace et al., DNA Damage–Inducible Transcripts in Mammalian Cells; *Proc. Natl. Acad. Sci. U.S.A.*, 85:8800–8804 (1988).

Fornace et al., Mammalian Genes Coordinately Regulated by Growth Arrest Signals and DNA–Damaging Agents; *Mol. Cell Biol.*, 9:4196–4203 (1989).

Bargonetti et al, Wild–Type But Not Mutant p53 Immunopurified Proteins Bind to Sequences Adjacent to the SV40 Origin of Replication; *Cell.*, 65:1083–1091 (1991).

Chemical Abstracts, vol. 117, No. 7, issued 17 Aug. 1992 (Columbus, Ohio USA) B.D. Price et al. "Gadd45 and Gadd153 messenger RNA levels are increased during hypoxia and after exposure of cells to agents which elevate the levels of the glucose–hypoxia and after exposure of cells to agents which elevate the levels of the glucose–regulated proteins." p. 561, abstract No. 67442y and *Cancer Res.* (1992) 52:3814–3817.

Chemical Abstracts, vol. 115, No. 11, issued 16 Sep. 1991 (Columbus, Ohio USA) M.A. Papathanasiou et al. "Induction by ionizing radaition of the gadd45 gene in cultured human cells: lack of mediation by protein kinase C." p. 419, abstract No. 109459a and *Mol. Cell. Biol.* (1991) 11:1009–1016.

Chemical Abstracts, vol. 101, No. 19, issued 05 Nov. 1984 (Columbus, Ohio USA), D. Wolf et al. "Reconstitution of p53 expression in a nonproducer Ab–MuLV–transformed cell line by transfection of a functional p53 gene." p. 153, abstract No. 164671z and *Cell* (1984) 38:199–226.

(List continued on next page.)

*Primary Examiner*—Stephanie W. Zitomer
*Assistant Examiner*—Eggerton Campbell
*Attorney, Agent, or Firm*—Morgan & Finnegan, L.L.P.

[57] ABSTRACT

The dependence of ionizing radiation-induced GADD45 mRNA expression on the presence of functional p53 in mammalian cells is disclosed. First and second oligonucleotide sequences are provided which can form a double-stranded oligomer capable of binding to functional p53 protein. The present invention demonstrates that the dependence of ionizing radiation-induced GADD45 mRNA expression on the presence of functional p53 and the binding of functional p53 to a double-stranded oligomer binding sequence can serve as the basis for methods for determining the presence of functional p53 in mammalian cell lines and tumors.

12 Claims, 3 Drawing Sheets

OTHER PUBLICATIONS

Kern, et al., "Identification of p53 as a Sequence–Specific DNA–Binding Protein." Science, 252: 1708–1711 (1991).

Kern et al., "Oncogenic Forms of p53 Inhibit p53–Regulated Gene Expression." Science, 256: 827–830 (1992).

Funk et al., "A Transcriptionally Active DNA–Binding Site For Human p53 Protein Complexes." Mol. Cell. Biol., 12: 2866–2870 (1992).

El–Deiry et al., "Definition of a Consensus Binding Site for p53."

Kastan et al., "Participation of p53 Protein in the Cellular Response to DNA Damage." Cancer Res. 51:6304–6311 (1991).

Kuerbitz et al., "Wild–Type p53 Is A Cell Cycle Checkpoint Determinant Following Irradiation." Proc. Natl. Acad. Sci. U.S.A., 89:7491–7495 (1992).

Fornace et al., "DNA Damage–Inducible Transcripts In Mammalian Cells." Proc. Natl. Acad. Sci. U.S.A., 85:8800–8804 (1988).

Fornace et al.,"Mammalian Genes Coordinately Regulated by Growth Arrest Signals and DNA–Damaging Agents." Mol. Cell Biol., 9:4196–4203 (1989).

Papathanasiou et al., "Induction by Ionizing Radiation of the gadd45 Gene in Cultured Human Cells: Lack of Mediation by Protein Kinase C." Mol. Cell Biol. 11: 1009–1016(1992).

Bargonetti et al., "Wild–Type but Not Mutant p53 Immunopurified Proteins Bind to Sequences Adjacent to the SV40 Origin of Replication." Cell, 65:1083–1091 (1991).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TGGTACAGAA   CATGTCTAAG   CATGCTGGGG                                30
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CCCCAGCATG   CTTAGACATG   TTCTGTACCA                                30
```

METHODS FOR DETERMINING THE PRESENCE OF FUNCTIONAL P53 IN MAMMALIAN CELLS

This is a continuation of application Ser. No. 07/974,960, filed on Nov. 12, 1992 now abandoned.

FIELD OF THE INVENTION

This invention is in the field of tumor cell biology. More specifically, this invention relates to the first identification of a gene, GADD45, whose expression has been shown to be altered by the presence of functional p53 protein and to the development of methods for determining the presence of functional p53 protein in mammalian cells.

BACKGROUND OF THE INVENTION

The p53 protein was first detected in a complex with the SV40 large T antigen in rodent cells transformed by simian virus SV40 (Lane, D. P. et al. (1979) *Nature*, 278:261–263). Subsequently, p53 was shown to be complexed with adenovirus and oncogenic papillomavirus oncoproteins (Sarnow, P. et al. (1982) *Cell*, 28:387–394; Werness, B. A. et al. (1990) *Science*, 248:76–79). Initially, p53 protein was considered to be a cellular proto-oncogene but recent observations have indicated that the gene encoding p53 in its native form is a tumor suppressor gene. Experimental support for the role of p53 as a tumor suppressor has been provided by the demonstration that the p53 gene can suppress the growth of transformed murine or human cells and that mutation or deletion of the p53 gene results in loss of this suppressor function (Eliyahn, D. et al. (1989) *Proc. Natl. Acad. Sci. U.S.A.*, 86:8763–8767; Baher, S. J. et al. (1990) *Science*, 249:912–915; Mercer, W. E. et al. (1990) *Proc. Natl. Acad. Sci. U.S.A.*, 87:6166–6170). To date, such mutations of the p53 gene have been demonstrated in tumors of the colon, breast, lung, ovary, bladder, and several other organs, making the p53 gene the most commonly mutated gene yet identified in human cancers (Vogelstein, B., (1990) *Nature*, 348:681–682). Based on the association of tumor progression with alterations in the p53 gene, major research efforts have been devoted to elucidating the potential biological function of p53.

Recent evidence strongly suggests that one function of p53 protein may be in the regulation of gene transcription. Several groups have demonstrated sequence-specific binding of p53 to DNA (Bargonetti et al. (1991) *Cell*, 65:108314 1091); Kern et al. (1991) *Science*, 252:1708–1711) and a genomic consensus sequence has been elucidated that consists of two copies of a symmetric 10 base pair (bp) motif separated by 0–13 bp (El-Deiry et al. (1992) *Nature Genet.*, 1:45–49). Placement of this consensus sequence adjacent to a basal promoter linked to chloramphenicol acetyltransferase (CAT) or luciferase reporter genes resulted in induction of the reporter gene when these constructs were cotransfected with a p53 expression vector into mammalian cells (Kern et al. (1992) *Science*, 256:827–830; Funk W. D. et al. (1992) *Mol. Cell. Biol.*, 12:2866–2871). In addition, the amino-terminus of p53 has been shown to behave as an acidic transcriptional activation domain when fused to GAL4 (Fields, S. et al. (1990) *Science*, 249:1046–1049).

More recently, wild-type (wt) p53 protein has been shown to directly activate transcription in vitro (Farmer, G. et al. (1992) *Nature*, 358:83–86). However, despite the experimental evidence supporting a role for p53 protein in transcriptional activation and the high interest in the potential involvement of p53 in tumorigenesis, there are currently only a few methods available for determining the presence of wt or mutant p53 protein in mammalian cells. One widely used method involves laborious DNA sequencing of the p53 gene itself. A major drawback of this approach is that the presence of a normal p53 DNA sequence is not necessarily an accurate predictor of the presence of functional p53 protein in the cells assayed since interference of p53 function by viral proteins or by abnormal binding of p53 protein to endogenous cellular proteins can occur (Momand, J. et al. (1992) *Cell*, 69:1237–1245; Oliner, J. D. et al. (1992) *Nature*, 358:80–83). In addition, this approach is both costly and time-consuming.

Another method used for determining the presence of wt or mutant p53 involves the use of antibodies capable of distinguishing between these two forms of p53. However, this approach also has several limitations. First, many of the mutations which arise in the p53 protein are point mutations and not all such mutations would be expected to be distinguished by a limited number of antibodies. Second, since p53 is the most commonly mutated protein identified in human cancers, the number of antibodies necessary to detect all of the different mutant forms of p53 may be quite high; therefore, this method would be impractical and costly. Finally, the use of anti-p53 antibodies to determine the presence of functional p53 in the cell is not an accurate predictor of functional p53 presence for the reasons cited above for the DNA sequencing method. Therefore, while currently used assays can detect the presence of wild-type or mutant p53 protein in mammalian cells, they cannot accurately determine the presence of functional p53 protein in these cells.

One potential approach to developing a method for determining the presence of functional p53 protein in mammalian cells would be to identify a specific gene whose expression is dependent on the presence of functional p53. Recent studies demonstrating a role for p53 protein in the G1 arrest of the cell cycle following damage of DNA by ionizing radiation (Kastan, N. B. et al. (1991) *Cancer Res.*, 51:6304–6311; Kuerbitz, S. J. et al. (1992) *Proc. Natl. Acad. Sci. U.S.A.*, 89:7491–7495). These studies suggested that genes that are differentially regulated after DNA damage and growth arrest may be candidates for p53-inducible genes.

Five gadd (growth-arrest and DNA-damage inducible) genes have been isolated on the basis of induction after DNA-damage in Chinese hamster ovary (CHO) cells. Subsequently, these genes were found to be induced by DNA-damaging agents or other treatments eliciting growth-arrest, such as serum reduction, in a wide variety of mammalian cells (Fornace, A. J. et al. (1989a) *Mol. Cell. Biol.*, 9:4196–4203). In particular, the GADD45 and GADD153 genes have been found to be rapidly and coordinately induced by agents such as methyl methanesulfonate (MMS) that produce high levels of base damage in DNA in every cell line examined, including human, hamster, murine, and rat cells (Fornace, A. J. et al., (1989a); Fornace, A. J. et al. (1992) *Ann. N. Y. Acad. Sci.*, 26:505–524). Recently, the human GADD45 gene was found to be rapidly induced by ionizing radiation (IR) in lymphoblasts and fibroblasts (Papathanasiou, M. A. et al., (1991) *Mol. Cell Biol.*, 11:1009–1016)). This IR response appeared to be distinct from the "gadd" response to MMS and other base-damaging agents because only GADD45 was strongly induced, and induction occurred with doses of IR that produced relatively little DNA base damage. In addition, a recent report (Fornace, A. J. et al. (1991) in Chapman, J. D., Dewey, W. C., Whitmore, G. F. (eds): "In Radiation Research: A Twentieth- Century Perspective", Academic Press, San Diego, p. 213) demonstrated that IR induction of GADD45 is absent in some human tumor cell lines. Taken together, this information suggests a potential role for p53 in the IR response of GADD45.

SUMMARY OF THE INVENTION

The invention includes two methods for determining the presence of functional p53 protein in mammalian cells. The first method is for determining the presence of functional p53 in mammalian cells by measuring GADD45 mRNA expression.

In the second method, two nucleic acid sequences are utilized. The first nucleic acid sequence has the sequence according to SEQ ID No. 1 and the second has the sequence according to SEQ ID NO. 2. SEQ ID NO. 1 and SEQ ID NO. 2 are complementary sequences found in the third intron of the human GADD45 gene and SEQ ID NO. 1 and SEQ ID NO. 2 can form a double-stranded nucleic acid sequence capable of binding to functional p53 protein. The presence of functional p53 protein in mammalian cells is determined by measuring binding of mammalian cell protein extracts with the double-stranded nucleic acid sequence.

DETAILED DESCRIPTION OF THE INVENTION

Figure 1A:
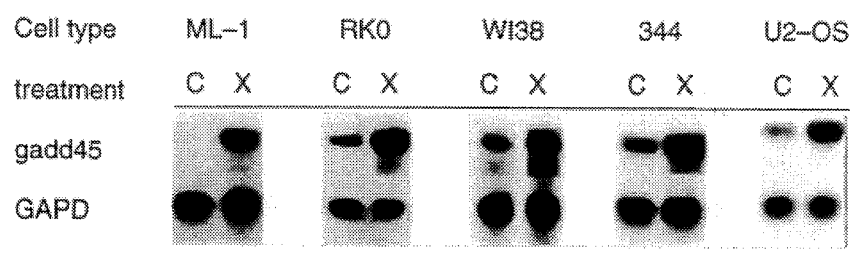
FIGS. 1A–C show the relationship of p53 phenotype to the γ-ray response of GADD45. A. RNA from γ-irradiated (X) and unirradiated (C) human cell lines with a wtp53 phenotype were analyzed by RNase protection assay using probes complementary to human GADD45 and glyceraldehyde-3-phosphate dehydrogenase (GAPD) mRNA. B. Human tumor cell lines with a mutant or null p53 phenotype were analyzed as in (A). C. Primary fibroblasts from mice with the designated p53 genotype were irradiated as above and RNA was analyzed by Northern blot using probes complementary to hamster GADD45 and β-actin mRNA.

The present invention relates to identification of GADD45 as a gene whose expression has been shown to be altered by the presence of functional p53 protein in mammalian cells. "Functional p53 " means p53 protein which is able to activate gene transcription. More specifically, the invention relates to the identification of GADD45 as a gene that is up-regulated by p53 after treatment of mammalian cells with a specific inducing signal, especially ionizing radiation. The invention further relates to a method of determining the presence of functional p53 protein in mammalian cells based on the dependence of IR-induced GADD45 mRNA expression on the presence of functional p53.

In one embodiment of the invention, the method to detect functional p53 comprises:

(a) stimulating mammalian cells to increase expression of GADD45 mRNA; and (b) comparing the level of GADD45 mRNA in stimulated cells to the level of GADD45 mRNA in unstimulated cells.

Examples of mammalian cells that can be used in the present invention are transformed mammalian cell lines. Such cell culture lines include, but are not limited to, cells of lymphoblast and fibroblast origin. A preferred cell line is the ML-1 lymphoblast cell line. (Kastan, M. B. et al. (1991b) *Cancer RES.,* 51:4279–4286)

In this invention, primary cultures of mammalian cells can also be used. Such cells can be biopsies taken from mammalian tumors, where tumor cells include, but are not limited to, tumor cells of the colon, lung, breast, ovary and bladder. Mammalian cell cultures can be initiated from biopsies by surgical incisional or excisional methods. A preferred method of initiating cell culture lines is via the removal of viable tumor tissue under sterile conditions. In most cases, a needle biopsy containing about $10^6$ to about $10^8$ cells is sufficient to initiate a culture. It is understood by one skilled in the art that the number of tumor cells required to initiate and establish a cell culture line depends on the individual tumor to be examined. In a preferred embodiment, certain tumor cells are cultured short-term (2 days to 20 days) using standard cell and tissue culture techniques ("Selected Methods in Cellular Immunology" (1980) Mishell, B. B. and Shügi, S. M. (eds) W. H. Freeman and Company, San Francisco) until about $10^7$ or more cells are obtained. Analysis of the cellular material can then be carried out by the above-mentioned method. For the purpose of the invention described herein, "mammalian" includes, but is not limited to, humans, monkeys, dogs, mice, hamsters and rats.

In another embodiment, the stimulation of cells in step (a) of the above-mentioned method comprises irradiating the cells for a time period and with a dose of ionizing radiation sufficient to induce or stimulate GADD45 mRNA expression. Ionizing radiation (IR) as used herein comprises a photon beam from a linear accelerator or gamma-radiation emitted by various radioisotopes. A preferred source of IR is gamma-irradiation emitted by a$^{137}$ cesium gamma-irradiator. Doses of IR effective to induce GADD45 mRNA expression range from about 2–20 Gray (Gy). A preferred time period and dose of IR effective to induce GADD45 mRNA expression is 20 Gy. Following IR stimulation cells are left in culture for about 1 to about 4 hours, preferably about 3 hours, prior to harvesting for use in the method. One skilled in the art will appreciate that various radiomimetic compounds (e.g. bleomycin) and DNA-damaging agents can also be used to stimulate the cells (Fornace, A. J. et al. (1992) *Annual Rev. of Genetics,* 26:505–524)

In step (b) of the method, RNA can be isolated from irradiated mammalian cells as whole cell RNA or as poly(A)$^+$ RNA. Whole cell RNA can be isolated by methods known to those skilled in the art. Such methods include extraction of RNA by differential precipitation (Birnboim, H. C. (1988) *Nucleic Acids Res.,* 16:1487–1497), extraction of RNA by organic solvents (Chomczynski, P. et al. (1987) *Anal. Biochem.,* 162:156–159) and extraction of RNA with strong denaturants (Chirgwin, J. M. et al. (1979) *Biochemistry,* 18:5294–5299). Poly(A)$^+$ RNA can be selected from whole cell RNA by affinity chromatography on oligo-d(T)

columns (Aviv, H. et al. (1972) *Proc. Natl. Acad. Sci.*, 69:1408–1412). A preferred method of isolating RNA is extraction of whole cell RNA by acid-phenol (Chomczynski et al. 1987).

The methods for determining levels of cellular GADD45 mRNA expression to be compared in step (b) include Northern blotting (Alwine, J. C. et al. (1977) *Proc. Natl. Acad. Sci.*, 74:5350–5354), dot and slot hybridization (Kafatos, F. C. et al. (1979) *Nucleic Acids Res.*, 7:1541–1522), filter hybridization (Hollander, M. C. et al. (1990) *Biotechniques;* 9:174–179), RNase protection (Sambrook, J. et al. (1989) in "Molecular Cloning, A Laboratory Manual", Cold Spring Harbor Press, Plainview, N.Y.) and polymerase chain reaction (Watson, J. D. et al. (1992) in "Recombinant DNA" Second Edition, W. H. Freeman and Company, New York). A preferred method is the RNase protection assay.

The GADD45 nucleic acid sequence used as a probe for determining GADD45 mRNA expression is substantially homologous to human GADD45 cDNA (Papathanasiou et al. (1991) *Mol. Cell. Biol.*, 11:1009–1016). By "substantially homologous" is meant a level of homology between the nucleic acid sequence and the human GADD45 cDNA sequence. Preferably, the level of homology is in excess of 70%, more preferably in excess of 80%, with a particularly preferred nucleic acid sequence being in excess of 90% homologous with the human GADD45 clone.

The nucleic acid sequence can be labeled in single-stranded or double-stranded form. Labelling of the GADD45 nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:126–131; Erickson, P. F. et al. (1982) *J. of Immunology Methods*, 51:241–249; Matthaei, F. S. et al. (1986) *Anal. Biochem.*, 157:123–128) and methods which allow detection by fluorescence using commercially available products. A preferred method of labelling the GADD45 nucleic acid sequence is by synthesizing a $^{32}$p-labelled RNA probe by in vitro transcription of double-stranded GADD45 nucleic acid sequence using [$\alpha$-$^{32}$P]UTP (Melton, D. A. et al. (1984) *Nucleic Acids Res.*, 12:7035–7056). The size of the probe can range from about 75 nucleotides to about 800 nucleotides. A preferred probe size is 269 nucleotides, spanning positions 296–565 of the human GADD45 cDNA (Papathanasiou et al. 1991).

The present invention also provides a purified and isolated nucleic acid sequence having SEQ ID NO. 1 and a purified and isolated nucleic acid sequence having SEQ ID No. 2. SEQ ID NO. 1 and SEQ ID NO. 2 are complementary sequences found in the third intron of the human GADD45 gene and are set forth below:

SEQ ID NO. 1
TGGTACAGAA CATGTCTAAG CATGCTGGGG

SEQ ID NO. 2
CCCCAGCATG CTTAGACATG TTCTGTACCA

In a preferred embodiment, SEQ. ID NO. 1 and SEQ ID NO. 2 are synthetic oligonucleotides. Those skilled in the art would be aware that oligonucleotides can be synthesized by automated instruments sold by a variety of manufacturers or can be commercially custom-ordered and prepared.

In a preferred embodiment, SEQ ID NO. 1 and SEQ ID NO. 2 form a labelled, double-stranded nucleic acid sequence which binds to functional p53 and which is purified and isolated. The first and second strands can be labelled by using radiolabelled ATP and T4 polynucleotide kinase, radiolabelled nucleotides, and Klenow enzyme, (Sambrook, J. et al. (1989) in "Molecular Cloning, a Laboratory Manual", Cold Spring Harbor Press, Plainview, N.Y.) or by using any of the above-mentioned non-radioactive methods. A preferred method of labelling employed [$\gamma$-$^{32}$p] ATP and T4 kinase (Sambrook, J. et al. (1989)). SEQ ID NO. 1 and SEQ ID NO. 2 can anneal with each other to form double-stranded nucleic acid sequence by heating a mixture of the two sequences to 60°–90° C. for 5 to 30 minutes followed by cooling over 20 minutes to one hour to room temperature. A preferred method of annealing involves heating SEQ ID NO. 1 and SEQ ID NO. 2 at 65° C. for 5 minutes followed by slow cooling to room temperature over 30 minutes. The order of the labelling and annealing steps is not fixed; annealing can precede labelling or vice versa.

The present invention also relates to a method for determining the presence of functional p53 in mammalian cells by measuring binding of mammalian cell protein extract to a double-stranded nucleic acid sequence the previously-described said sequence comprising SEQ. ID NO. 1 and SEQ ID NO. 2, comprising:

(a) stimulating mammalian cells;

(b) binding the double-stranded nucleic acid sequence to protein extract prepared from stimulated and unstimulated cells; and (c) detecting complexes of protein extract bound to the double-stranded nucleic acid sequence.

A preferred stimulus of mammalian cells is ionizing radiation. Doses of ionizing radiation that can be used in this method range from about 5 to about 20 Gy. A preferred dose of ionizing radiation is 20 Gy. Following IR stimulation, cells are left in culture for about 1–4 hours, preferably about 3 hours, prior to harvesting for use in the method.

In one embodiment, the binding reaction of step (b) of the method can include from about 0.005 Ci to about 0.05 ci of labelled double-stranded nucleic acid sequence and from about 2 to about 20 μg of protein extract. In a preferred embodiment, the binding reaction includes 0.005 Ci of labelled double-stranded nucleic acid sequence and 10 μg of protein extract. Types of protein extracts which are preferred are nuclear extracts (Dignam, J. D. et al. (1983) *Nucleic Acids Res.*, 11:1475–1489, Carrier, F. et al. (1992) *Mol. Cell. Biol.*, 12:1856–1863).

The binding of double-stranded nucleic acid sequence to protein extract can occur from 10 minutes to 2 hours at about 4° C. –37° C. Preferred conditions are for 20 minutes at room temperature. Methods useful to detect complexes of protein extract bound to double-stranded oligomer include mobility-shift analysis, Southwesterns, and immunoprecipitation (Sambrook, J. et al, (1989); Ausubel, J. et al, (1987) in "Current Protocols in Molecular Biology", John Wiley and Sons, New York). A preferred method is mobility-shift analysis using the double-stranded nucleic acid sequence labelled with [$\gamma$-$^{32}$ p] ATP and T4 kinase. For mobility shift analysis, the protein extract-oligomer complexes can also be detected by using labelled protein extract, wherein the cells can be metabolically labelled with $^{125}$I, $^{35}$S, biotin and various fluorescent labels prior to the preparation of the protein extract.

The invention also provides a diagnostic kit for determining the presence of functional p53 in mammalian cells. This diagnostic kit comprises a purified and isolated nucleic acid according to SEQ ID NO. 1 and a purified and isolated nucleic acid sequence according to SEQ ID NO. 2.

Any articles or patents referenced herein are incorporated by reference. The following examples illustrate various aspects of the invention but are in no way intended to limit the scope thereof.

Materials

The materials used in the following Examples are as follows:

Cell Lines

Embryonic fibroblasts from mice with manipulated p53 genes were obtained and characterized as previously described (Livingstone L. R. et al, (1992) *Cell*, 70:923–935). Other cell types utilized were previously described (Kastan et al, (1991a); Kuerbitz, et al, (1992)).

Plasmid Clones

The following cDNA clones were used: pXR45m, a nearly full-length Chinese hamster gadd45 clone (Papathanasiou et al, (1991) and pA2, a 1.2 kb Chinese hamster β-actin clone. The plasmid pGAPD4 contained an insert spanning positions 256–359 of the human glyceraldehyde-3-phosphate dehydrogenase cDNA (GenBank/EMBL Accession No. M17851) that was subcloned between the HindIII and EcoRI sites of pGEM7zf. The plasmid pRibo-Hg45 consisted of a 269 bp fragment spanning positions 296–565 of the human gadd45 cDNA (Papathanasiou et al, (1991) that was subcloned between the EcoRI and SmaI sites of pBluescript II SK.

EXAMPLE 1

Dependence of Induction of GADD45 mRNA by Ionizing Radiation on the Presence of Functional p53

The GADD45 gene has previously been found to be inducible by ionizing radiation (IR) in normal human fibroblasts and lymphoblasts but not in some tumor cell lines (Papathansiou, M. A. et al., (1991)). In an effort to identify genes that may be induced by p53 after ionizing radiation, the response of the GADD45 gene was examined in human cells where the p53 phenotype is known. Human cell lines with a wild-type p53 phenotype (FIG. 1A) or a mutant or null p53 phenotype (FIG. 1B) or primary fibroblasts from mice with the designated p53 genotype (FIG. 1C) were maintained in culture and exposed to 20 Gy of ionizing radiation for 3 hours prior to harvest as previously described (Kastan, M. B. et al. (1991a); Kuerbitz, S. J. et al. (1992) *Proc. Natl. Acad. Sci.*, 89:7491–7495). Cells were harvested by lysing them in 4M guanidine thiocyanate. Whole-cell RNA was then isolated by the acid phenol method (Chomczynski, P. et al. (1987)).

Figure 1B:
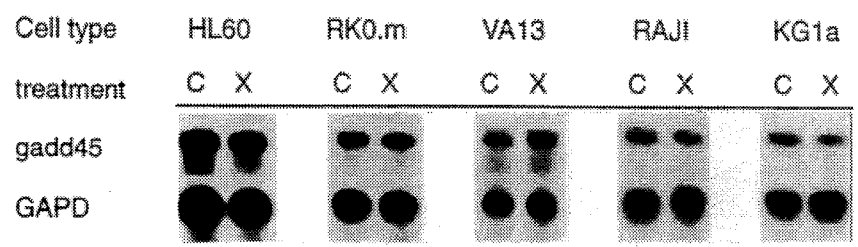
Figure 1C:
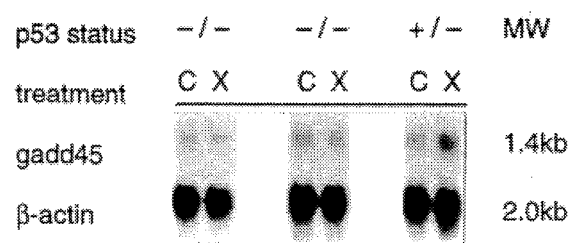
Figure 2A:
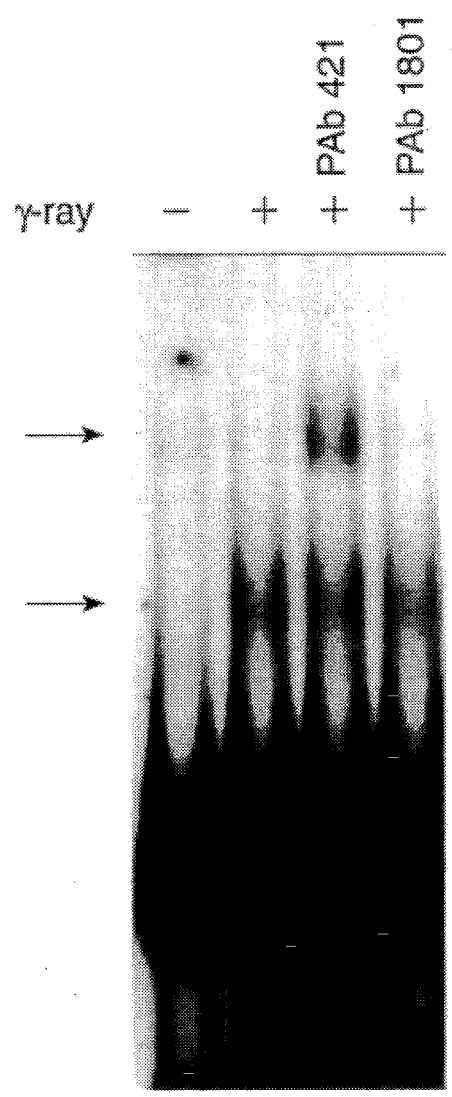
FIGS. 2A and 2B show mobility-shift assays with a double-stranded oligomer containing a p53-binding site and nuclear extracts from irradiated cells. A. Nuclear extracts from irradiated or unirradiated ML-1 cells were incubated with labeled DNA corresponding to the human GADD45 p53-binding site, and the resulting DNA-protein complexes were electrophoresed in a neutral acrylamide gel and visualized by autoradiography. B. In a separate experiment, a similar analysis was carried out using nuclear extracts from irradiated or unirradiated ML-1 or HL-60 cells. The first 3 lanes consist of controls where probe alone (lanes 1 and 2) or probe with antibody to p53 (lane 3) were used in the absence of nuclear extracts. The lower arrow indicates the position of the IR-induced band and the upper arrow indicates the position of the super-shifted band seen with the antibody to -53, PAb421.
Figure 2B:
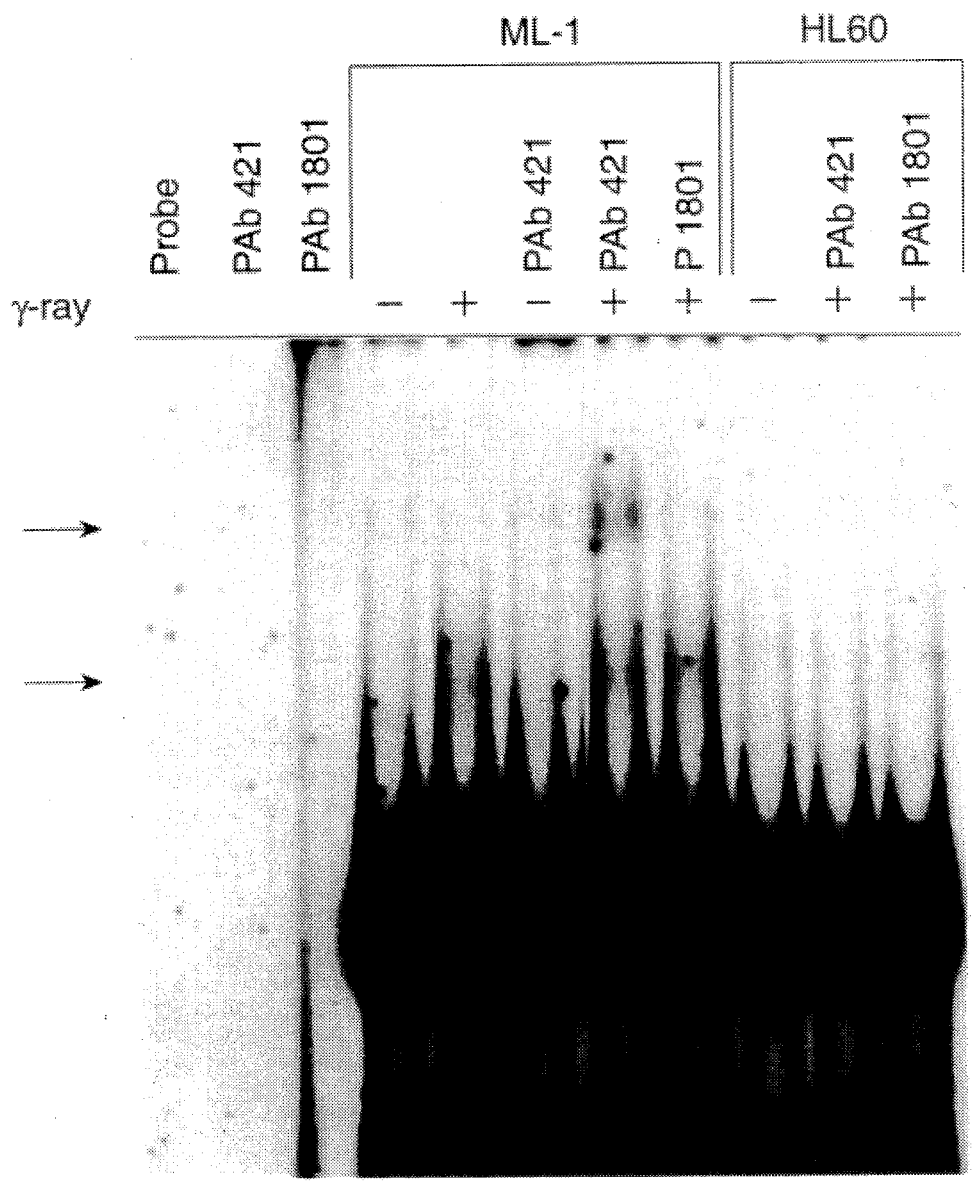

For FIGS. 1A and 1B, isolated RNA was analyzed by RNase protection assays. Reagents for these assays were obtained from Ambion, Inc., and the procedure was similar to that supplied by the manufacturer with only minor modifications. In brief, the plasmids pRibo-Hg45 and pGAPD4 were linearized with HindIII or BamHI respectively, and in vitro transcription was carried out at 4° C. for 1 hr with T3 or T7 RNA polymerase, respectively. GADD45 and GAPD riboprobes were labeled with [α-$^{32}$P]UTP at 14 or 15 Ci/mmol, respectively. 10 µg of whole-cell RNA was hybridized with both riboprobes simultaneously (in the same test tube) at 53° C. for 15 hr and then digested with RNase A and RNase T1. Following proteinase K digestion and phenol/chloroform extraction, the samples were analyzed on a 8M urea/5% acrylamide gel. Protected bands were visualized by autoradiography and were quantified with a Betascope (Betagen, Inc.). The relative level of GADD45 mRNA was determined by normalizing the Betascope counts (minus background) for GADD45 to that of GAPD for each sample.

When mRNA levels were determined in this fashion, a clear increase for GADD45 was observed in cells with a wild-type p53 phenotype while the control transcript GADD was unchanged (FIG. 1A). In contrast, appreciable induction GADD45 of GADD45 mRNA was not evident in cells lacking a wild-type p53 phenotype (FIG. 1B).

Analysis of the RNA isolated from primary fibroblasts (FIG. 1C) was done by Northern blot since RNAse protection requires a homologous probe and the only rodent probe available for GADD45 is from hamster. In brief, samples of whole cell RNA (10 µg) were size separated and hybridized with a hamster GADD45 probe; the blot was stripped and then hybridized with a hamster β-actin probe (Fornace, A. J. et al., (1989b)). Only the hybridizing bands are shown with the estimated sizes (Kb) to the right. The results clearly show that an increase in GADD45 mRNA levels following IR treatment failed to occur in the murine embryonic fibroblasts in which the p53 genes had been disrupted by homologous recombination (p53 status −/−) while the heterozygous cells with only one intact wild-type p53 allele still remaining (p53 status +/−) still induced GADD45 mRNA following IR treatment (NOTE: +/+ cells were not available in sufficient quantities for this experiment). Thus, the dependence of the induction of GADD45 mRNA by ionizing radiation on the presence of wild-type p53 is observed not only in cells of hematopoietic origin (FIG. 1A) but also in non-hematopoietic cells such as fibroblasts.

EXAMPLE 2

Relationship of p53 Functional Status to GADD45 Induction in Cell Lines Having Normal or Abnormal p53 Function In order to further examine the relationship of p53 functional status to GADD45 mRNA induction, the magnitude of this induction was measured in numerous cell lines having normal p53 function (8 cell lines) or abnormal p53 function (7 cell lines).

TABLE 1

| Fold increase of GADD45 mRNA after γ-irradiation | | | | |
|---|---|---|---|---|
| Cell Line | Cell type | p53 status | γ-ray $G_1$ arrest[a] | Relative Abundance of mRNA[b] |
| Normal p53 function | | | | |
| ML-1 | myeloid Leukemia | wt/wt | + | 9.9 |
| U2-OS | osteosarcoma | wt/wt | + | 3.0 |
| AG1522 | skin fibroblast | wt/wt | ND | 4.2 |
| 344 | skin fibroblast | wt/wt | + | 3.3 |
| WI38 | lung fibroblast | wt/wt | ND | 2.0 |
| RKO | colorectal carcinoma | wt/wt | + | 3.1 |
| RKO.cp[c] | colorectal carcinoma | wt/wt | + | 3.2 |
| RKO.c[d] | colorectal carcinoma | wt/wt | + | 4.1 |
| Abnormal p53 function | | | | |
| RKO.m[e] | colorectal carcinoma | wt/wt, cut | − | 1.4 |
| Raji | lymphoid leukemia | wt/mut | − | 0.7 |
| SW480 | colorectal carcinoma | mut/— | − | 1.4 |

TABLE 1-continued

Fold increase of GADD45 mRNA after γ-irradiation

| Cell Line | Cell type | p53 status | γ-ray G$_1$ arrest[a] | Relative Abundance of mRNA[b] |
|---|---|---|---|---|
| KG1a | myeloid leukemia | mut/— | — | 0.8 |
| HL60 | myeloid leukemia | —/— | — | 1.0 |
| VA13 | lung fibroblast | ?, SV40 transformed | ND | 1.0 |
| HeLa | cervical carcinoma | wt/wt, HPV-18 infected | ±[f] | 1.6 |

[a]Activation of arrest in the G$^1$ phase of the cell cycle following γ-irradiation as published previously (Kastan et al., (1991a); Kuerbitz et al., 1992); ND, not tested.
[b]Relative values for samples harvested 4 hr. after 20 Gy compared to untreated controls as determined by RNAse protection assay (see Experimental Procedures).
[c]Polyclonal population, transfected with control vector lacking p53 gene insert (Kuerbitz et al, 1992)
[d]Clonal population, transfected with control vector lacking p53 gene insert (Kuerbitz et al, 1992)
[e]Clonal population, transfected with mp53 vector (RKO.p53.13; Kuerbitz et al, 1992)
[f]Measurable decrease in S-phase, but markedly less than cells with normal p53 function All cell lines were cultured and treated with 20 Gy ionizing radiation 3 hours prior to the harvest of the cells as described previously (Kastan, M. B. et al. (1991), Kuerlitz, S. J. et al. (1992)). Total RNA was isolated and analyzed by RNAse protection assay as described in Example 1. This analysis was done in a blinded fashion with the identity of the cell types withheld until all quantitations were completed.

The relative abundance of GADD45 mRNA in irradiated cells was estimated by first normalizing to the value for GAPD in each sample and then dividing this value for irradiated cells by that of its control. Normal lymphoblasts and fibroblasts, and tumor cells with a wt p53 status all exhibited greater than 2-fold increases in GADD45 mRNA after irradiation, with a range up to 10-fold. Induction of GADD45 mRNA also correlated with the activation by ionizing radiation of the G$_1$ checkpoint in these cells, which have normal p53 function (Kastan, M. B. et al. (1991), Kuerbitz, S. J. et al. (1992)). In contrast, cells with mutant (SW480, Raji, and KG1a) or absent (HL60) p53 genes failed to show appreciable induction of GADD45 mRNA after IR (Table 1). Loss of GADD45 responsiveness after IR also correlated with loss of the G$_1$ checkpoint (Table 1) and loss of induction of p53 protein (Kastan, M. B. et al. (1991a), Kuerbitz, S. J. et al. (1992)).

The basal levels of GADD45 mRNA did not correlate with p53 status and were low in all cells. It was estimated that the abundance of GADD45 mRNA was >100-fold lower than that of GAPD mRNA in these cell lines. The relative levels of GAPD mRNA could be accurately estimated by quantitative dot-blot hybridization using whole-cell RNA and normalized to the polyA content of the cells. When this was done (data not shown), this value was used to compute the relative level of GADD45 mRNA in different cell types (also employing the values in Table 1), and to confirm that the level of GAPD mRNA remained constant after IR.

Cells with wt p53 genes, but expressing viral products that interfere with p53 function, similarly lacked normal IR-mediated GADD45 induction. VA13 is a derivative of WI38 that was obtained by transformation with SV40 (Girardi, A. J. et al. (1966) Ann. Med. Exp. Biol. Fern., 44:242–254). The T antigen of this virus is known to bind to p53 protein (Lane, D. P. et al. (1979)), and VA13 cells were deficient in induction of GADD45 mRNA (Table 1). Hela cells have been infected with HPV-18 which contains an E6 protein that inhibits normal p53 function (Werness, B. A. et al. (1990), Scheffner, M. et al. (1990) Cell, 63:1129–1136; Scheffner, M. et al. (1991) Proc. Natl. Acad. Sci, 88:5523–5527; Crook, T. et al. (1991) Cell, 67:547–556). Activation of the G$_1$ checkpoint and induction of GADD45 was substantially less in HeLa cells than in the cell lines with normal p53 function (Table 1).

To demonstrate that it was the status of the p53 gene and not some other difference between these cell lines which was responsible for the differences in gadd45 induction, gadd45 induction was evaluated in cells in which the p53 gene had been manipulated. RKO colorectal carcinoma cells stably overexpressing a mutant (codon 143) p53 gene have previously been shown to lose the G$_1$ arrest following IR (Kuerbitz, S. J. et. al. (1992)). In contrast to parental RKO cells (FIG. 1A) and RKO cells transfected with a control vector lacking the p53 gene insert, RKO cells overexpressing the mutant p53 allele did not significantly increase GADD45 mRNA levels following IR (Table 1).

Example 3

Demonstration of Binding of Endogenous p53 to a Double-Stranded Oligomer Containing a p53-Binding Element Found in the GADD45 Gene In order to determine whether endogenous p53 could bind to a double-stranded oligomer containing a conserved p53-binding sequence located in the 3rd intron of the human GADD45 gene, mobility-shift assays were carried out using a double-stranded oligonucleotide corresponding to a putative p53-binding site located in the third intron of the human GAAD45 gene and nuclear extracts from γ-irradiated cells. In brief, cells were irradiated with a $^{137}$cesium source at 5.5 Gy/min and nuclear extracts were prepared as described previously (Dignam et al, (1983); Carrier et al, 1992). DNA-binding reactions were carried out for 20 min at room temperature in a buffer containing 20 mM N-2-hydroxyethylpiperazine-M'-2-ethanesulfonic acid (HEPES) (pH 7.8), 100 mM KCl 1 mM EDTA, 1 mM dithiothreitol, 0.5 µg of sonicated salmon sperm DNA, $10^4$ dpm of labeled probe, 10% glycerol and 10 µg of nuclear protein extract. The probe used was a 30-mer double-stranded synthetic oligonucleotide comprising two synthetic oligonucleotides containing SEQ. ID. No. 1 and SEQ. ID. No. 2, respectively. Each oligonucleotide was radioactively labeled with [γ-$^{32}$p] ATP and T4 kinase (Sambrook, J. et al, (1989)) and the labelled oligomers were ethanol precipitated, washed with 70% ethanol and either allowed to auto-anneal or to anneal with each other by incubation at 65° C. for 5 minutes in 50 mM Tris, pH 7.6/10 mM MgCl$_2$/1 mM ATP/1 mM DTT/5% (w/v) polyethylene glycol-8000, followed by slow cooling over 30 minutes to room temperature. The annealed DNA was extracted with phenol/chloroform, ethanol precipitated, washed with 70% ethanol and resuspended in 3 mM Tris, pH 7.5/0.2M EDTA. Where indicated, 0.2 µg of monoclonal anti-p53 antibodies (commercially available) (PAb421 or PAb1801) were added prior to the addition of nuclear extract. PAb421 IgG was purified from ascites fluid on protein-A agarose (ImmunoPure Plus, Pierce, Rockford, IL); PAb1801 IgG (Oncogene Science, Manhasset, N.Y.) was used directly. The samples were then analyzed on a 4% non-denaturing acrylamide gel (Carrier et al, 1992).

The results show that in extracts from unirradiated ML-1 cells, several bands are evident—some of which may represent constitutive DNA-binding proteins; however, a distinct band (lower arrow, FIG. 3A) which is clearly visible in the IR extract is not detected in the extract from untreated cells. With the inclusion of the PAb421 antibody to p53, a higher "super-shifted" band is observed (upper arrow). Interestingly, as was found previously (Funk, W. D. et al. (1992)) with other p53-binding oligomers and p53 protein produced by an expression vector, the p53 antibody PAb1801, which binds to the amino terminus of p53 protein (in contrast to the carboxyl terminal binding of PAb421 (Wade-Evans, A. et al. (1985) *Embo. J.*, 4:699–706), did not produce a super-shifted band. The reason for this difference in the antibodies is uncertain. In a second similar experiment (FIG. 3B), results without nuclear extracts and with extracts from HL60 cells were compared to those from ML-1 cells. In contrast to ML-1 cells, neither the induced band or the super-shifted band are apparent in extracts from irradiated HL60 cells, which have a null p53 genotype. In addition to using the antibodies and the HL-60 cells, the specificity of p53 binding in these experiments was further demonstrated by blocking both shifted bands with addition of excess unlabeled identical oligomer (data not shown). These results indicate that an IR-inducible nuclear factor, which binds to the GADD45 p53 site, is present in ML-1 cells, and that this factor contains p53. This is the first demonstration of binding of an endogenous p53 gene product to a specific DNA sequence.

EXAMPLE 4

Determination of the Functional Status of p53 in MammaLian cell Tumors

The functional status of p53 in mammalian cells can be determined by measuring increases in cellular GADD45 mRNA levels after ionizing radiation and/or binding of endogenous p53 to a double-stranded oligomer containing a conserved p53-binding element found in the human GADD45 gene. Biopsies of lymphoid and myeloid tumors from laboratory were obtained by surgical excision or incision. Primary cultures of mammalian cells can be initiated from biopsies by removal of adequate amounts of viable tumor tissue under sterile conditions. The number of cells required to initiate one or more cell culture lines is determined empirically for each tumor but in many cases, a needle biopsy containing about $10^6$ to about $10^8$ cells is sufficient. Once the cell culture lines are initiated, they can be grown on a short-term basis (from about 2 days to about 20 days) using standard culture techniques ("Selected Methods in Cellular Immunology", (1980) Mishell, B. B. and Shiigi, S. M. (eds), W. H. Freeman and Company, San Francisco). About $10^7$ or more cells from such cultures are necessary to allow direct determination of the presence of functional p53 in these tumor cells by stimulation with ionizing radiation as described in Example 1. Whole cell RNA is isolated and analyzed by RNase protection assay in order to determine whether GADD45 mRNA increased in response to the ionizing radiation. An observed increase in GADD45 mRNA in stimulated vs. unstimulated tumor cells indicates that functional p53 is present in the tumor cells while no change in the levels of GADD45 mRNA indicates that the tumor cells exhibit abnormal p53 function.

Alternatively, tumor cell culture lines can be analyzed for the presence of functional p53 by mobility-shift analysis as described in Example 3 of nuclear extracts prepared from these cultures. About $10^7$ or more cells is adequate for preparation of nuclear extract.

---

---

We claim:

1. A method for determining the presence of functional p53 in mammalian cells by measuring GADD45 mRNA expression, said method comprising the steps of (a) stimulating the mammalian cells with ionizing radiation or with a radiomimetic compound to increase GADD45 mRNA expression; and (b) comparing the level of GADD45 mRNA in said stimulated cells to the level of GADD45 mRNA in unstimulated cells.

2. The method of claim 1, wherein said stimulating step includes the step of irradiating said cells with a dose of ionizing radiation sufficient to stimulate GADD45 mRNA expression.

3. The method of claim 2, wherein the dose of ionizing radiation sufficient to stimulate GADD45 mRNA expression is 2–20 Gy.

4. The method of claim 1, wherein the comparison step includes the steps of:

(a) providing a labelled GADD45 nucleic acid sequence probe; and (b) contacting the GADD45 mRNA with said probe.

5. The method of claim 4, wherein said comparison step further includes the step of isolating RNA from the stimulated and unstimulated cells.

6. A purified and isolated oligonucleotide having a sequence according to SEQ ID No. 1.

7. A purified and isolated oligonucleotide having a sequence according to SEQ ID No. 2.

8. A purified and isolated oligonucleotide capable of binding functional p53, said oligonucleotide comprising SEQ ID No. 1 and SEQ ID No. 2, respectively.

9. A method for determining the presence of functional p53 in mammalian cells by measuring binding of mammalian cell protein extract to an oligonucleotide capable of binding p53, said oligonucleotide having a sequence contained in the GADD45 gene; said method comprising the steps of:

(a) stimulating the mammalian cells with ionizing radiation or with a radiomimetic compound to increase GADD45 mRNA expression;

(b) contacting the protein extract from stimulated and unstimulated cells with said oligonucleotide capable of binding p53; and (c) detecting complexes of said protein extract which bind to said oligonucleotide.

10. The method of claim 9, wherein said stimulating step includes the step of irradiating said cells with a dose of ionizing radiation from 5–20 Gy.

11. The method of claim 10, wherein said oligonucleotide of step (b) is a purified and isolated oligonucleotide comprising SEQ ID No. 1 and SEQ ID No. 2.

12. A diagnostic kit for detecting the presence of functional p53 in mammalian cells, said kit comprising a purified and isolated oligonucleotide having a sequence according to SEQ ID No. 1 and a purified and isolated oligonucleotide having a sequence according to SEQ ID No. 2.

* * * * *